(12) United States Patent
Geywitz et al.

(10) Patent No.: US 11,452,004 B2
(45) Date of Patent: Sep. 20, 2022

(54) METHOD FOR WIRELESS DATA TRANSMISSION RANGE EXTENSION

(71) Applicant: KONINKLIJKE PHILIPS N.V., Eindhoven (NL)

(72) Inventors: Hansjoerg Geywitz, Kusterdingen (DE); Markus Wohlschlager, Sindelfingen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 302 days.

(21) Appl. No.: 16/346,965

(22) PCT Filed: Nov. 1, 2017

(86) PCT No.: PCT/EP2017/077948
§ 371 (c)(1),
(2) Date: May 2, 2019

(87) PCT Pub. No.: WO2018/086972
PCT Pub. Date: May 17, 2018

(65) Prior Publication Data
US 2019/0261220 A1    Aug. 22, 2019

(30) Foreign Application Priority Data
Nov. 8, 2016    (EP) .................................... 16197643

(51) Int. Cl.
*H04W 28/06* (2009.01)
*G16H 40/67* (2018.01)
(Continued)

(52) U.S. Cl.
CPC ............ *H04W 28/06* (2013.01); *G16H 40/67* (2018.01); *H03M 7/30* (2013.01); *H03M 7/3059* (2013.01);
(Continued)

(58) Field of Classification Search
CPC ....... H04W 28/06; H04W 4/80; H04W 4/023; G16H 40/67; H03M 7/30; H03M 7/3059;
(Continued)

(56) References Cited

U.S. PATENT DOCUMENTS 4,524,244 A    6/1985 Faggin
4,633,465 A * 12/1986 Fitch .................... H04L 25/067
                                                                 375/227

(Continued)

FOREIGN PATENT DOCUMENTS

| EP | 2001234 | 12/2008 | |
|----|---------|---------|---|
| EP | 2040499 | 3/2009 | |
| KR | 20120090470 A * | 8/2012 | ........... A61B 8/4427 |

OTHER PUBLICATIONS

Mao et al: "Wireless sensor network localization techniques", Computer Networks, Elsevier, Amsterdam, NL, vol. 51, No. 10, May 6, 2007.

(Continued)

*Primary Examiner* — Franklin D Balseca (57) ABSTRACT

The present disclosure relates to apparatuses and a method for wireless health monitoring comprising dynamically adjusting sound data compression level and/or transmission bandwidth of transmission between a mobile transmitter and a receiver. In some embodiments, a method for wireless health monitoring may include calculating (202) a distance between a mobile transmitter (104) and a receiver (110). A data compression (108) level for compressing a signal, e.g., a sound signal, from the transmitter may be determined out of a plurality of data compression levels based on the distance between the transmitter and the receiver. A transmission bandwidth may then be determined (208) based at least in part on the determined data compression level. The (Continued)

compressed signal may be transmitted (210) using the determined transmission bandwidth.

18 Claims, 5 Drawing Sheets

(51) Int. Cl.
  *H03M 7/30* (2006.01)
  *H04B 11/00* (2006.01)
  *H04Q 9/00* (2006.01)
  *H04W 4/80* (2018.01)
  *H04L 69/04* (2022.01)
  *H04W 4/02* (2018.01)
  *A61B 5/00* (2006.01)
  *A61B 8/00* (2006.01)

(52) U.S. Cl.
  CPC .............. *H04B 11/00* (2013.01); *H04L 69/04* (2013.01); *H04Q 9/00* (2013.01); *H04W 4/023* (2013.01); *H04W 4/80* (2018.02); *A61B 5/0002* (2013.01); *A61B 5/4343* (2013.01); *A61B 8/4472* (2013.01); *H04Q 2209/40* (2013.01)

(58) Field of Classification Search
  CPC .......... H04B 11/00; H04L 69/04; H04Q 9/00; H04Q 2209/00; H04Q 2209/40; H04Q 2209/80; H04Q 2209/84; A61B 8/4472; A61B 8/4477; A61B 8/4483; A61B 8/4494; A61B 8/46; A61B 8/52; A61B 5/0002; A61B 5/001; A61B 5/0011; A61B 5/0013; A61B 5/0015; A61B 5/002; A61B 5/0022; A61B 5/0026; A61B 5/4343; A61B 2560/0271
  See application file for complete search history.

(56) References Cited

U.S. PATENT DOCUMENTS

| | | | |
|---|---|---|---|
| 5,699,404 A | 12/1997 | Satyamurti | |
| 7,207,941 B2 | 4/2007 | Sharf | |
| 7,733,373 B2* | 6/2010 | Akiyama | H04L 1/0001 348/192 |
| 8,452,239 B2* | 5/2013 | Kohno | H04L 1/206 455/72 |
| 9,100,307 B2 | 8/2015 | Hoctor | |
| 9,454,321 B1* | 9/2016 | Smaldone | G06F 3/0653 |
| 9,802,316 B2* | 10/2017 | Koselka | G01L 5/009 |
| 10,158,534 B2* | 12/2018 | Acharya | H04W 4/38 |
| 10,278,581 B2* | 5/2019 | Gaster | A61B 5/02411 |
| 10,709,425 B2* | 7/2020 | Waechter-Stehle | G06T 7/10 |
| 10,860,687 B2* | 12/2020 | Cohen | A61B 5/0004 |
| 2008/0298461 A1* | 12/2008 | Lee | H04N 21/4621 375/240.01 |
| 2009/0080536 A1* | 3/2009 | Lee | H04L 65/80 375/240.26 |
| 2012/0253847 A1 | 10/2012 | Dell | |
| 2013/0151260 A1 | 6/2013 | Francois | |
| 2015/0164477 A1* | 6/2015 | Ryu | G01S 7/52033 600/443 |
| 2016/0157717 A1 | 6/2016 | Gaster | |
| 2018/0278979 A1* | 9/2018 | Ahmed | H04L 47/263 |

OTHER PUBLICATIONS

Boos et al: "A New, Lightweight Fetal Telemetry System" Hewlett-Packard Journal 1995.
Boatin et al: "Wireless Fetal Heart Rate Monitoring in Inpatient Full-Term Pregnant Women: Testing Functionality and Acceptability" PLoS One, Jan. 26, 2015.
GE Healthcare, Mini Telemetry System, 2016.
Taylor et al: "Towards multi-patient leadless and wireless cardiotocography via RF telemetry", Medical Engineering & Physics 20 (1998) 764-772.
International Search Report and Written Opinion dated Feb. 8, 2018, for International Application No. PCT/EP2017/077948 filed Nov. 1, 2017.

* cited by examiner

METHOD FOR WIRELESS DATA TRANSMISSION RANGE EXTENSION

CROSS REFERENCE TO RELATED APPLICATIONS

This application is the U.S. National Phase application under 35 U.S.C. § 371 of International Application No. PCT/EP2017/077948, filed Nov. 1, 2017 published as WO 2018/086972 on May 17, 2018, which claims the benefit of European Patent Application Number 16197643.6 filed Nov. 8, 2016. These applications are hereby incorporated by reference herein.

BACKGROUND OF THE INVENTION

Radio waves, like sound waves, become weaker as they propagate away from their source. The strength of radio waves that arrive at a given location, by direct or indirect paths, is equal to the strength of the original source minus the amount of loss due to distance (inverse square loss), material attenuation loss, and reflection losses. In general, the higher the frequency the greater the loss. After many reflections radio waves become weaker and essentially non-directional. They ultimately contribute to ambient radio noise. The strength of ambient radio noise is relatively constant in a given area, that is, it does not diminish with distance. Radio noise is generally considered to be undesirable.

A system's transmission range is a function of a favorable level of the desired transmission compared to the level of undesirable transmissions and noise. EP 2 001 234 A1 discloses to transmit uncompressed data as long as the distance between transmitter and receiver is below a predetermined threshold and compress data according to a predetermined compression algorithm if the distance between transmitter and receiver exceeds the predetermined threshold. Ultimately, the receiver must be able to pick up a usable signal from the transmitter. Here, "useable" means that the strength of the desired signal is within the sensitivity range of the receiver and is sufficiently stronger than, or different from, undesirable signals and RF noise to produce an acceptable S/N ratio at the audio output of the receiver.

Wireless data transmission is becoming more ubiquitous in medical settings. In fetal monitoring, for example, wireless data monitoring allows a pregnant patient to move without being encumbered by cables, which enhances the birthing process. At the beginning of each fetal monitoring session, the ultrasound transducer has to be placed on the abdomen of the mother for a localization of the fetal heart. During this procedure it is important to have the best possible sound quality for getting the optimum position and therefore the highest signal quality. But as the mother moves away from the monitor, listening to the fetal heart sound details becomes less important because the mother herself probably does not hear the fetal heart sounds beyond a certain distance between the sound signal transmitter and receiver (and a nurse is not likely in the mother's hospital room, either). Also, while the patient with a wireless monitor walks down a hospital hallway, for example, additional background noise in the sound channel increases. In such a case, transmitting the highest quality sound data may be less important.

US Patent Application No. 2016/0157717 discloses a wireless pregnancy monitor that includes a patch worn on the patient's skin and an electromyography ("EMG") sensor and fetal heart rate ("FHR") sensor. The wireless monitor further includes a wireless transmitter that transmits the EMG and FHR signal to a remote device. Taylor et al., *Med. Eng. Phys.* 1998, Vol. 10, pp. 764-72 discloses a prototype wireless cardiotocography comprising ultrasound and tocodynamometer transducers. Data compression is achieved by extracting the Doppler ultrasound signal envelope and representing the frequency content of the signal using a zero crossing counting technique. The RF-based system uses time division multiplexing and data compression to permit the use of up to 10 units to be used at the same frequency in the same area.

SUMMARY OF THE INVENTION

The present disclosure relates to techniques for dynamically adjusting a sound data compression level and/or a transmission bandwidth of wireless health monitoring transmissions allowing a dynamic adjustment, in particular an extension, of the radio frequency transmission range. In one example embodiment, a method may include: calculating a distance between a mobile transmitter and a receiver based on one or more attributes of a wireless communication channel between the transmitter and the receiver; determining a data compression level out of a plurality of data compression levels for compressing data to be transmitted from the transmitter to the receiver based on the distance between the transmitter and the receiver; compressing the data to be transmitted based on the determined data compression level; determining, based at least in part on the determined data compression level, a transmission bandwidth; and transmitting the compressed data in a signal from the transmitter to the receiver using the determined transmission bandwidth.

In various embodiments, the data may represent a detected sound signal. In various embodiments, the method may further include rendering, by the receiver, synthetic audio in lieu of the sound signal in response to a determination that the determined data compression level satisfies a threshold. In various embodiments, the method may further include rendering, by the receiver, synthetic audio in lieu of the sound signal in response to a determination that a predetermined number of bit errors are detected by the receiver.

In various embodiments, a data compression level for a current transmitter-receiver distance may be selected from a previously-stored reference compression level corresponding to a transmitter-receiver distance closest to the current transmitter-receiver distance. In various embodiments, the transmission of the compressed data may be terminated when one or more bit errors are detected by the receiver.

In various embodiments, calculating the distance between the transmitter and the receiver may include analysing a received signal strength ("RSS") of the signal. In various embodiments, calculating the distance between the transmitter and the receiver may include analysing a time of flight ("TOF") of the signal. In various embodiments, determining the transmission bandwidth may include selecting one or more sub-bands from a plurality of sub-bands based on the determined data compression level. In various embodiments, transmitting the compressed data may include transmitting the compressed data from the transmitter to the receiver using the selected one or more sub-bands.

In various embodiments the method further comprises prior to calculating a distance between a transmitter and a receiver: detecting a sound signal using a device; performing a dynamic range compression of the detected sound signal;

digitizing the dynamically compressed sound signal to obtain a digitized sound signal.

In addition, some implementations include an apparatus including memory and one or more processors operable to execute instructions stored in the memory, where the instructions are configured to perform any of the aforementioned methods.

In various embodiments, an apparatus for wireless health monitoring is provided. The apparatus is portable by a patient to be monitored and comprises a transmitter and a processor configured to calculate a distance between the transmitter and a receiver based on one or more attributes of a wireless communication channel between the transmitter and the receiver, determine a data compression level out of a plurality of data compression levels for compressing data to be transmitted from the transmitter to the receiver based on the distance between the transmitter and the receiver, compress the data to be transmitted based on the determined data compression level, and determine, based at least in part on the determined data compression level, a transmission bandwidth, wherein the transmitter is configured to transmit the compressed data in a signal to the receiver using the determined transmission bandwidth.

In various embodiments, the apparatus comprises a sound detector to detect a sound signal, wherein the processor is further configured to perform a dynamic range compression of the detected sound signal, and to digitize the dynamically compressed sound signal to obtain a digitized sound signal prior to calculating a distance between a transmitter and a receiver.

In various embodiments, the apparatus further comprises a memory for storing a plurality of reference compression levels corresponding to respective transmitter-receiver distances wherein the processor is configured to select the data compression level from the plurality of reference compression levels by selecting the reference compression level corresponding to a transmitter-receiver distance closest to the current transmitter-receiver distance.

In various embodiments, the transmitter is configured to transmit data indicative of the determined data compression level to the transceiver together with the digitized sound signal.

In various embodiments, the apparatus is a wireless ultrasound transducer.

In various embodiments, a health monitor base station is provided that comprises a receiver to receive a compressed data signal representative of a sound signal from a health monitoring transducer, wherein a data compression level of the compressed data signal is selected from a plurality of data compression levels, and a processor configured to render synthetic audio in lieu of the sound signal (i) in response to a determination that the data compression level satisfies a predetermined threshold, or (ii) in response to a determination by the receiver that a predetermined number of bit errors is detected.

Some implementations also include a non-transitory computer readable storage medium storing computer instructions executable by one or more processors to perform any of the aforementioned methods.

It should be appreciated that all combinations of the foregoing concepts and additional concepts described in greater detail herein are contemplated as being part of the subject matter disclosed herein. For example, all combinations of claimed subject matter appearing at the end of this disclosure are contemplated as being part of the subject matter disclosed herein.

BRIEF DESCRIPTION OF THE DRAWINGS

The accompanying drawings, which are included to provide a further understanding of the disclosure, are incorporated herein to illustrate embodiments of the disclosure. Along with the description, they also serve to explain the principle of the disclosure. In the drawings.

DETAILED DESCRIPTION OF EMBODIMENTS

The present disclosure describes health monitoring using wireless ultrasound transducers wherein a mother is able to move around while undergoing fetal heart monitoring. For example, while wearing wireless transducers configured with selected aspects of the present disclosure, the mother can move freely inside or outside a room in such a way that the wireless ultrasound transducer can transmit signals using data compression levels and/or transmission bandwidths that can be altered as the mother moves farther away from the monitor. In this way, optimum signal quality can be obtained by dynamically adjusting compression levels and/or transmission bandwidths (e.g., based on a dynamically determined compression level) to be used for the received signal depending on the patient's distance from the monitor. By using, for example, a higher compression level as the patient's distance from the monitor increases, narrower transmission bandwidths can be used. By using narrow transmission bandwidths, the likelihood of signal interference by and to other devices can be reduced.

The stronger the signal connecting a base station to a wireless monitoring device (e.g., a wireless ultrasound transducer), the stronger the connection between the base station and the wireless monitoring device, which allows high data rates. But as a patient with a wireless monitoring device moves away from the base station acting as the receiver, the signal strength decreases and the effect of any interference sources in the vicinity is magnified. For example, some of the transmitted data packets may not reach the receiver, thus forcing the wireless monitoring device to redo the transmission. In accordance with the present disclosure, the wireless monitoring device and the base station use reduced bandwidths as the patient moves farther from the base station to maintain data transmission reliability over the connection. With a reduced bandwidth, the carrier to noise ("C/N") ratio is enhanced, which results in higher transmission coverage range. Another advantage of using a narrower bandwidth when a wireless monitoring device moves away from the base station is a decreased likelihood of signal interference to other radio-frequency ("RF") systems, and vice versa.

Figure 1:
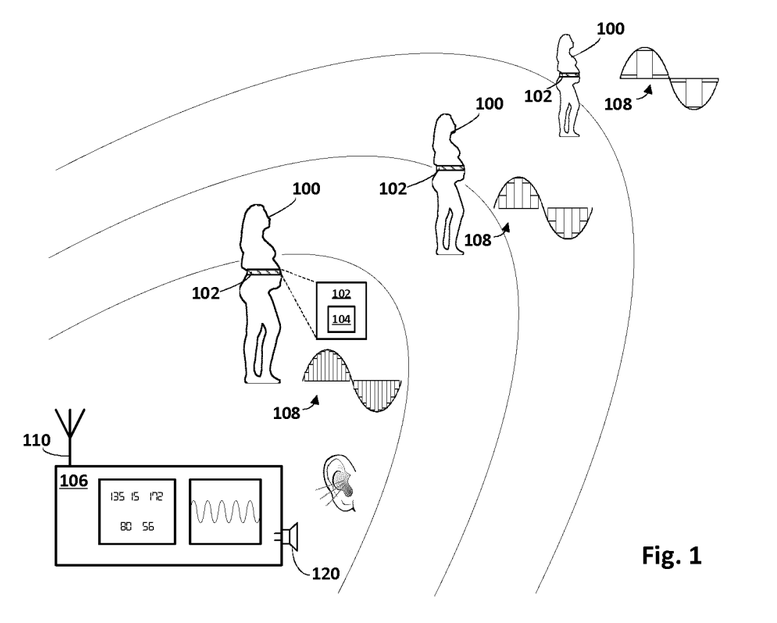
FIG. 1 is one example embodiment of the disclosure illustrating a method for extending radio frequency range by adjusting the transmitted sound signal quality.

FIG. 1 illustrates one example embodiment of the present disclosure. In this embodiment, a pregnant patient 100 is undergoing monitoring using a wireless ultrasound transducer 102, which is attached to the patient 100, and which includes a transmitter 104. A base station 106 (e.g., a fetal monitor) may include one or more receivers 110 to receive one or more signals from transmitter 104, as well as an audio transducer such as a speaker 120 to render audio data carried in the signal received from transmitter 104. As the patient 100 moves away from the base station 106, the data compression level 108 used in the sound data transmission may be adjusted (e.g., increased) based on the current distance between the transmitter 104 and the base station 106. The transmission bandwidth may also be altered (e.g., decreased) based on the data compression level 108 used.

In some embodiments, the farther the patient 100 travels from the base station 106 (e.g., a fetal heart rate monitor), the higher the compression level 108 the system uses. As a result, the bandwidth used for sound data transmission is successively reduced. The highest compression level 108 is reached when the received fetal heart sound quality has substantially degraded although it can still be identified as such. This corresponds to the smallest bandwidth possible and the system's maximum effective operating distance. One non-limiting way to determine that this point has been reached is when, for example, bit errors are detected during sound data transmission. At this distance from the base station 106, it may be the case that only the beat-to-beat heart activity value, without any sound information, can be reliably transmitted. At this distance and bandwidth, the base station 106 (base station or monitor) may simply play a synthetic audio (e.g., a beat or click sound) in lieu of the actual fetal heart beat sound with a repetition frequency that reflects the fetal heart rate reading.

Figure 2:
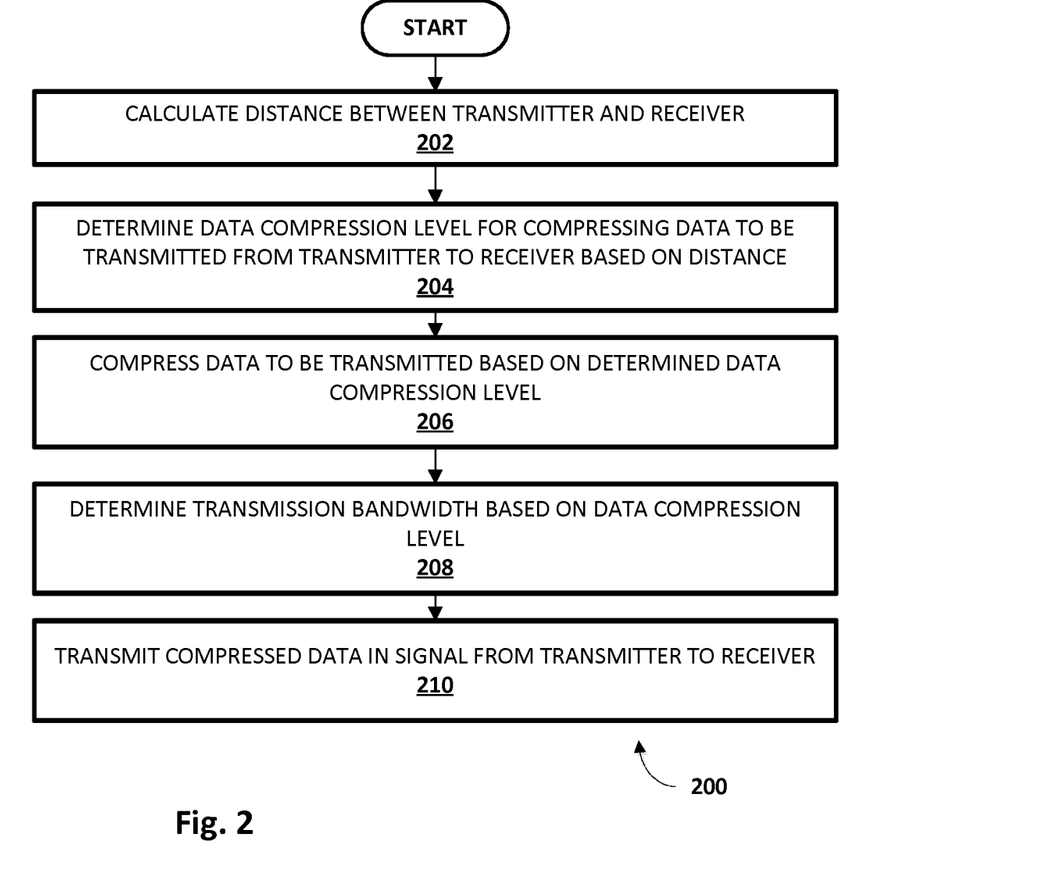
FIG. 2 is a flowchart illustrating a process according to one example embodiment of the present disclosure.

FIG. 2 is a flowchart illustrating one example embodiment of a method 200 for extending radio frequency transmission range. At block 202, the distance between a transmitter 104 (e.g., of wireless transducer 102) and a receiver 110 (e.g., of base station 106) may be calculated, e.g., based on one or more attributes of a wireless communication channel between the transmitter 104 and the receiver 110. Based on the calculated transmitter-to-receiver distance, at block 204, a data compression level for compressing data (e.g., detected audio data such as a fetal heartbeat) to be sent from the wireless transducer 102 to the base station 106 may be determined based at least in part on the distance between the wireless transducer 102 and the base station 106 calculated at block 202. At block 206, the data may be compressed based on the determined data compression level. At block 208, a transmission bandwidth may be determined based on the compression level used at block 206. At block 210, the system (e.g., wireless transducer 102) may transmit the compressed data in a signal from the transmitter to the receiver using the determined transmission bandwidth.

Figure 3:
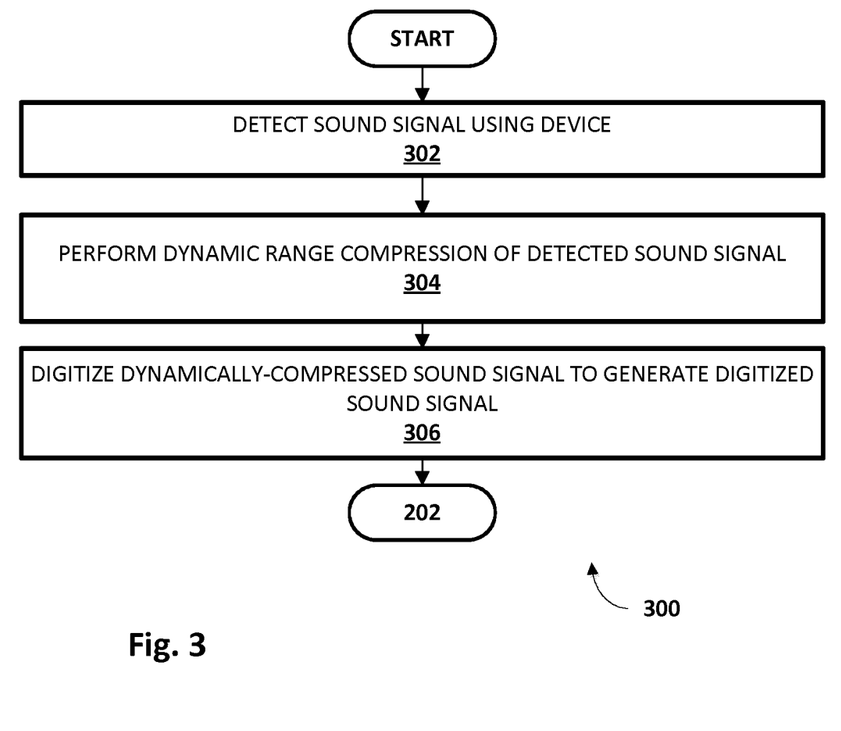
FIG. 3 is a flowchart illustrating a process according to another example embodiment of the present disclosure.

FIG. 3 is a flowchart illustrating an example method for detecting a sound such as a fetal heart beat and preparing the audio data for transmission, e.g., using the method 200 of FIG. 2. At block 302, a sound signal may be detected using a device such as wireless transducer 102 (which may be, for instance, an ultrasound transducer). At block 304, dynamic range compression may be performed on the detected sound signal (described in more detail below). At block 306, the dynamically compressed sound signal may be digitized to obtain a digitized sound signal. Method 300 may then proceed to block 202 and/or 208 of method 200. When dynamic range compression is performed prior to digitization, it may be necessary to communicate the compression level to the receiver. However, in other embodiments, the sound signal may be digitized first (block 306), and then dynamic data compression may be performed on the digitized sound signal.

It is possible that for the same absolute distance between the wireless transducer 102 and base station 106, different transmission bandwidths may be used to achieve optimal transmission. For example, this would be true in cases where a patient is roaming in a location where there are physical structures between the device and base station that attenuate the signal or where there are strong signal interference sources compared to another location from the same distance to the base station that has no or only weak signal interference source. This is because the speed of radio waves is somewhat slower when propagating through a medium other than a vacuum. Radio waves can also be affected by the size and composition of objects in their path. In particular, they can be reflected by metal objects if the size of the object is comparable to or greater than the wavelength of the radio wave. Large surfaces can reflect both low frequency and high frequency waves, but small surfaces can reflect only high frequency radio waves.

In one example embodiment of the present disclosure, wireless transducer 102 may be equipped with an audio digital signal processing ("DSP") circuit that is operable to optimize input audio data for transmission. Base station 106 may be equipped with a corresponding audio DSP circuit to optimize the output signal. In one embodiment, the input signal is digitized in the wireless transducer 102 and remains in digital form until output by base station 106, e.g., via speaker 120. The output from base station 106 to a digital equipment may also be in digital form. Non-limiting advantages of an all-digital wireless approach may include improved audio quality and/or improved radio transmission.

In one example embodiment of the present disclosure, an analog-to-digital ("A/D") converter may be used by wireless transducer 102 to convert a detected audio signal to a digitized audio signal. The resulting digitized audio signal (or a compressed version thereof) may be transmitted to base station 106. The digitized information may be demodulated and then converted back to analog form using a complementary digital-to-analog ("D/A") converter at base station 106.

In some embodiments, transmission bandwidths may be adjusted depending on the data compression level used, which in turn may be based on the transmitter-receiver distance. For purposes of the present disclosure, "bandwidth" may refer to, for instance, a range of frequencies and/or amplitudes available in a wireless communication channel to convey information. The bandwidth required for a high fidelity digital wireless system may depend on the amount of digital information transmitted. To deliver the highest quality audio signal in a practical digital wireless system, the transmitted data may be accommodated within allowable bandwidth limits using various techniques. In one example embodiment of the present disclosure, these techniques may be implemented by first coding the data in wireless transducer 102 and then decoding the transmitted data in base station 106.

In one example, a transmission coding scheme may include digitally dividing the full audio bandwidth into a number of sub-bands. Each sub-band may be processed separately to deliver the desired amount of data compression. The sub-band data may be assembled by wireless transducer 102 into a digital data stream which may be used to modulate transmitter output. In some embodiments, determining a transmission bandwidth to use for transmitting compressed audio data (block 208) may include selecting one or more sub-bands from a plurality of sub-bands based on the determined data compression level. The compressed data may then be transmitted from wireless transducer 102 to base station 106 using the selected one or more sub-bands. Depending on allowable bandwidth and other limitations, the modulation may utilize frequency-shift and/or phase-shift keying. In the base station 106, the incoming data stream may be disassembled into corresponding sub-band data. Each sub-band may be unpacked (e.g., decoded) to reproduce its original counterpart. Finally, the decoded sub-band data may be combined to reconstruct the original full-bandwidth audio signal. The process may be configured to achieve the highest audio quality and the lowest latency.

In some embodiments, the process of transmitting digital data in a radio signal may include modulating the carrier in discrete steps, e.g., using a process such as shift keying, e.g., frequency shift keying ("FSK"), amplitude shift keying ("ASK"), and/or phase shift keying ("PSK"). If the shift key signal has two possible values (e.g., corresponding to a bit value of "0" or "1") then the data rate may be equal to the bit rate. For example, a 2-FSK signal shifts between two possible frequencies where one frequency represents a "0" and the other a "1". However, it is possible to send more than one bit per cycle by coding multiple bits into "symbols". The symbol rate is equal to the bit rate divided by the number of bits transmitted with each symbol.

However, even with the reduced bandwidth requirements of higher order symbol coding techniques it still may not be practical to transmit the entire data stream within the available bandwidth. To reduce the data rate to manageable size, some form of data compression may be applied to the data to be transmitted from the wireless transducer 102 to the base station 106. Data compression schemes can be characterized as "lossless" or "lossy". A lossless scheme reduces the data stream by coding redundant data into shorter forms. Decoding "lossless" compressed data will exactly restore the entire original data stream. Lossless compression does not provide a high degree of compression on typical digital audio data. A lossy data compression scheme discards a certain amount of the original data stream, generally the least significant parts.

For audio data, such as that produced by a fetal heart monitor, various methods exist that rely on the characteristics and limitations of human audio perception. The best lossy compression schemes result in audio that is nearly indistinguishable from the original. However, each method involves a compromise between the degree of compression, audio quality, and processing time or latency. Each method has a bit rate that can be selected, the lowest allowing small data sizes with reduced fidelity and the highest offering improved audio fidelity at the expense of larger data sizes.

Another consideration for digital transmission systems is data transmission error. The integrity of the transmitted data stream can be adversely affected by radio interference, multi-path, and signal fading. The likelihood of errors also increases with the complexity of the transmission scheme. In one example embodiment of the present disclosure, various techniques that are well-known in the art are employed to minimize the effects of data loss.

In some embodiments, at least one sound data compression technique may be used in conjunction with dynamic range compression ("DRC") to further enhance the received signal quality. In the case of upward DRC, the volume of sounds below a preset threshold is amplified while leaving louder sounds unaltered. Downward DRC reduces loud sounds above a certain threshold while quiet sounds remain unaffected. Both downward and upward compression may reduce the dynamic range of an audio signal. The net result when dynamic range compression is applied along with a gain boost is that relatively soft or muted sounds become louder, while louder sounds remain unchanged. DRC may be accomplished in various embodiments through the use of compressors, which are dedicated electronic hardware units or audio software that performs DRC. Compressors may in some cases be available as software plugins that run in digital audio software, or as part of an embedded microcontroller.

As noted above, in some embodiments, when audio data is compressed, the compression level used may vary with the distance between the transmitting and receiving devices. For example, suppose a pregnant patient wearing a wireless ultrasound transducer 102 is walking down a hospital hallway away from a base station 106 while undergoing fetal heart monitoring. After a predefined time, the wireless transducer 102 may prepare to transmit data to the base station 106. Before transmitting, the distance between the wireless transducer 102 (or more particular, transmitter 104) and the base station 106 may be calculated. Various means of determining the distance between wireless transducer 102 and base station 106 are known in the art and may be used in embodiments of the present disclosure. For example, the distance between two wireless devices may be estimated using various attributes of a wireless communication channel between transmitter 104 and base station 106, such as RF received signal strength ("RSS"), which has been widely used due to simplicity. The RSS in free space decreases with the square of the distance between the transmitter and receiver, providing a one-to-one mapping from RSS to distance. Additionally or alternatively, an RF signal time-of-flight (TOF) may be measured between nodes to avoid many of the problems of RSS method.

After determining the distance between wireless transducer 102 and base station 106, the level of data compression to use may be determined based on the calculated distance between wireless transducer 102 and base station 106. In some embodiments, optimized sound data compression levels for different transmitter-to-receiver-distances may have been previously measured and stored in memory accessible to wireless transducer 102 and/or base station 106, e.g., for use in the selection of a compression level setting for a given calculated transmitter-receiver distance. In one example embodiment of the present disclosure, a combination of lossless and lossy algorithms that optimizes the tradeoff between acceptable signal quality and compression ratio may be used.

In one example, various reference compression ratios may be initially determined and optimized for sound quality for different corresponding transmitter-receiver distances. These initially determined reference compression ratios for different corresponding distances may be used to select an initial compression ratio to be used for subsequent actual pregnancy or fetal heart monitoring in which a monitored pregnant patient moves at various distances away from base station 106. The different initial compression ratios may be analyzed for sound quality as a function of line-of-sight distance from wireless transducer 102 to base station 106. In some embodiments, optimization of the various reference compression levels as a function of audio quality and transmitter-receiver distance may be performed up to a maximum distance in which only the beat-to-beat heart activity values, without any sound information, can be reliably transmitted. At this maximum distance (and minimum bandwidth), base station 106 may simply render a synthetic audio (e.g., a beat or click sound) in lieu of the actual fetal heart beat sound, with a repetition frequency that reflects the fetal heart rate reading.

Thus, in one example, for a given transmitter-receiver distance, a detected analog sound signal may be first inputted into the data compression system. A pre-compression data processor such as an A/D convertor may then convert the analog input data signal to digital input data. After digitizing the analog input data, the pre-compression data processor may divide the digitized input data into fixed length data packets. The length of each data packet may be chosen in some embodiments so that the data packets with higher data compression ratios do not yield substantially degraded audio quality compared to that of data packets with lower data compression ratios. Once at least a portion of the digital input data has been divided into fixed length data packets, at least one fixed length data packet may be stored in a memory. The memory may operate as a buffer that stores the at least one fixed length data packet until the at least one fixed length data packet can be processed by a first compression and encoding processor.

In one embodiment, one fixed length data packet may be held in the memory at any given time. Alternatively, multiple fixed length data packets may be held in the memory. Next, the at least one data packet may be processed by the first compression and encoding processor. When the first compression and encoding processor receives the at least one fixed length data packet from the memory, the at least one fixed length data packet is analyzed to determine the amount of data in the at least one fixed length data packet. Once the amount of data has been determined, the at least one fixed length data packet may be compressed using a previously-stored reference data compression ratio or level that corresponds most closely to the currently measured transmitter-receiver distance.

In another embodiment, the compressed, fixed length data packet may be transferred to a second compression and encoding processor. The second compression and encoding processor may convert the fixed length data packet into a variable length data packet by removing any unnecessary data bytes and leaving only the valid data bytes of the fixed length data packet. The resulting variable length, variable data compression ratio data packet is then transferred to the packet encoding processor. The packet encoding processor may insert a length code at one or both ends of the data packet. As described above, the length codes may contain at least information regarding the number of valid data bytes in the variable length, variable data compression ratio data packet.

After the length codes are added to the data packet, the data packet may be stored in the first memory and/or a second memory. The second memory may operate as a buffer that stores the variable compression ratio, variable length data packets until the variable compression ratio, variable length data packets can be output, e.g., via the output interface, to the receiver 110 as the output data signal. In another embodiment, the second memory stores the variable length, variable data compression ratio data packets until either the entire, or some portion, of the input data signal has been compressed using the data compression system. Alternatively, the second memory stores all of the output variable length, variable data compression ratio data packets as a data file. In another embodiment of the present disclosure, the input data signal is directly converted to variable data compression ratio, variable length data packets without being transformed to and from fixed length data packets.

In one example embodiment, wireless transducer 102 may monitor a patient's pregnancy or pregnancy-related status in various ways, such as by detecting a fetal heart rate ("FHR") signal using an FHR sensor selected from a Doppler ultrasound probe, an optical sensor providing a photoplethysmographic signal, and/or a set of electrodes providing an electrocardiographic ("EKG") signal. In another embodiment, pregnancy or pregnancy-related status of a patient may be monitored by wireless transducer 102 using a combined electromyography ("EMG") and FHR sensor devices. The EMG and FHR sensors may share at least a portion of a sensor circuit, and they may both be connected to and share use of a set of electrodes. Either or both of the EMG and FHR sensor devices may be, or may include, a Doppler ultrasound sensor.

Any other suitable device or sensor configured for detecting uterine contraction may be substituted for the EMG sensor, such as a device being generally referred to here as a uterine contraction monitor. One or both of the EMG and FHR sensors may be replaced by a Doppler ultrasound sensor. The Doppler ultrasound sensor may include an ultrasonic transducer/transmitter and a signal processor coupled to two or more ultrasound receiver/microphones.

In some embodiments, the combined EMG and FHR sensor devices may also include an inertial sensor configured for sensing fetal movement. In some such embodiments, the pregnancy status may be determined using the additional information from inertial motion signal from the inertial sensor. Additionally or alternatively, the patient's pregnancy status may be determined based on the inertial motion signal from the inertial sensor but excluding at least one of the EMG signal and the FHR signal. Additional sensors may include a temperature sensor for monitoring vital signs and providing notifications to the patient or medical personnel that the patient may have an infection based on, for example, a detected patient's elevated body temperature.

When a combined EMG/FHR sensors are used, the two sensors may be placed on a patient's abdomen. Then, monitoring and detection of EMG signal from the EMG sensor may be correlated in time to an FHR signal from the FHR sensor. In one embodiment, the EMG and FHR signals may be wirelessly transmitted to a remote device (e.g., base station 106) for processing and displaying the received signal. Of course, embodiments using EMG/FHR are only examples, and are not meant to be limiting. Other embodiments may employ the Doppler sound signal of an ultrasound sensor as described above.

Figure 4:
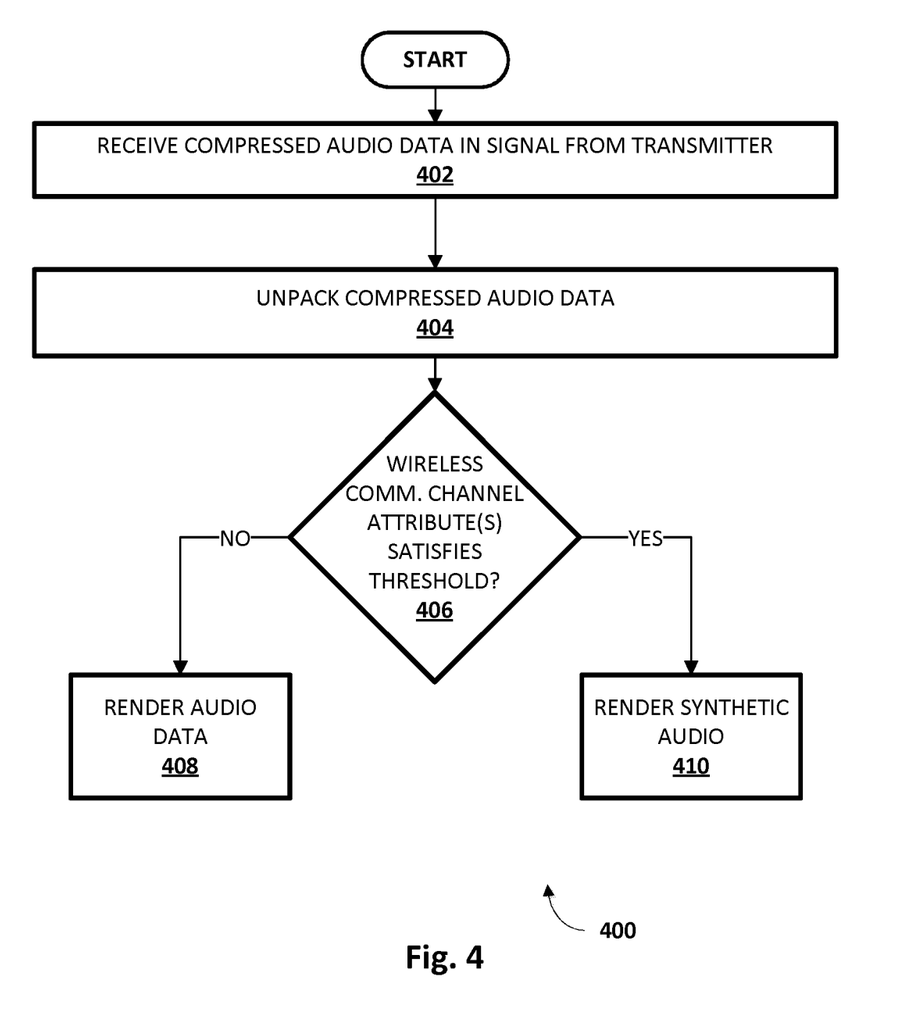
FIG. 4 is a flowchart illustrating a process according to another example embodiment of the present disclosure.

FIG. 4 depicts an example method 400 that may be performed, for instance, by base station 106, for rendering audio data received from wireless transducer 102. At block 402, base station 106 may receive compressed digitized audio data from transmitter 104 of wireless transducer 102. At block 404, base station 106 may unpack the compressed data. For example, depending on whether the compression used on the data was lossy or lossless, base station 106 may decode the compressed data to generate the original audio data or a close approximation thereof. Additionally or alternatively, unpacking the compressed data may include performing other operations such as error checking, e.g., detecting for bit errors.

In various embodiments, synthetic audio may be rendered in lieu of the sound signal in response to various signals. For example, at block 406 of FIG. 4, base station 106 may determine whether one or more attributes of a wireless communication channel between base station 106 and wireless transducer 102 satisfy one or more thresholds. For example, base station 106 may determine whether a calculated distance between wireless transducer 102 and base station 106 satisfies one or more thresholds, or whether a compression level employed by wireless transducer 102 satisfies one or more thresholds. In some embodiments, base station 106 may determine whether a number of bit errors detected during transmission satisfy one or more thresholds.

Whichever wireless communication channel attributes are examined, if base station 106 determines that they do not satisfy one or more thresholds, then method 400 may proceed to block 408, at which point base station 106 may render (e.g., using speaker 120) the audio data carried in the signal from wireless transducer 102. For example, the distance between base station 106 and wireless transducer 102 may not meet some maximum distance threshold (e.g., selected based on capabilities of the respective devices). As another example, the compression level employed by wireless transducer 102 may not satisfy a maximum compression threshold. As yet another example, less than a minimum threshold of error bits may be detected. Whichever the case, the audio signal between base station 106 and wireless transducer 102 may be sufficiently strong that it is possible to simply play the fetal heartbeat or other sound detected by wireless transducer 102.

On the other hand, if base station 106 determines that the one or more wireless communication channel attributes do satisfy one or more thresholds, then method 400 may proceed to block 410. At block 410, base station 106 may render synthetic audio in lieu of the actual audio signal received from wireless transducer 102. This may occur, for instance, when a compression level used by wireless transducer 102 is so great that the compressed audio data may not be decipherable or intelligible by a human ear, but yet may still carry an indication of a detected heartbeat. In such a situation, a synthetic heartbeat may be played instead.

Figure 5:
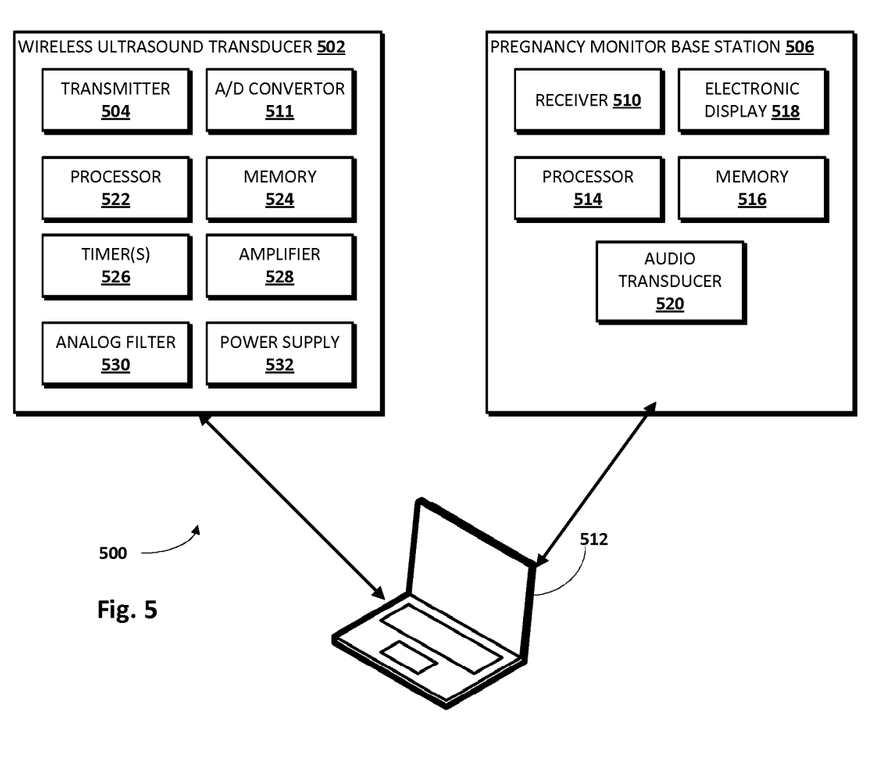
FIG. 5 is a block diagram according to the present disclosure illustrating a system used for extending radio frequency range by adjusting sound data compression level and transmission bandwidth.

FIG. 5 shows a block diagram of an example pregnancy monitoring system 500 that extends radio frequency transmission range by adjusting the transmitted signal sound quality. The pregnancy monitoring system 500 may include a wireless ultrasound transducer 502, which may correspond to wireless transducer 102 in FIG. 1. Wireless ultrasound transducer 502 may include a transmitter 504, e.g., for transmitting signals to a pregnancy monitoring base station 506. In various embodiments, wireless ultrasound transducer 502 may include any combination of uterus, heart, brain, and fetal monitors. In some embodiments, wireless ultrasound transducer 502 may include an analog-to-digital converter 511 connected to a plurality of electrodes for converting electrical signals corresponding to uterus, maternal and fetal heart and fetal brain signals into digital data.

Pregnancy monitoring base station 506 may include a receiver 510, and may be used to collect, analyze, and characterize uterine, maternal and fetal heart, or fetal brain activity data received from wireless ultrasound transducer 502. The monitor base station 506 of the pregnancy monitoring system 500 may further include a processor 514, memory 516, and an electronic display 518 coupled to processor 514 to display a patient's current pregnancy status based on, for instance, EMG and/or FHR signals received from wireless ultrasound transducer 502. In one embodiment, the base station 506 further includes an audio transducer 520 coupled to the electronic circuit. The audio transducer may be configured to provide an audible indication of the most recent pregnancy status, e.g., based on the EMG and FHR signals. In one example embodiment, the transducer 520 may include an audio speaker for emitting a tone or recorded message.

Either or both of wireless ultrasound transducer 502 and monitor base station 506 may communicate with one or more other computing devices 512, either through wired or wireless communication means, e.g., cellular, Bluetooth, ZigBee, infrared, or radio frequency.

In one example embodiment, the wireless transducer 502 may include a processor 522 that may be configured to execute, for example, a fetal movement detection algorithm. This makes it possible for wireless transducer 502 to transmit only a fetal movement detection bit (or other indication) instead of more detailed information such as the fetal movement Doppler signal, thereby saving RF channel transmission capacity. In some embodiments, the wireless transducer 502 may also include memory 524, such as a RAM and/or ROM, and one or more timers 526 that can run in several modes including timer, counter, pulse-width modulator, one-shot, free-running, or triggered from input pins or software. In some embodiments, the wireless transducer 502 may also include an independent watchdog timer and synchronous or asynchronous serial communication channels. Some of the timers (e.g., one in timer mode, two in one-shot mode) can be used to produce the gating signals for the pulsed ultrasound Doppler channel. Another set of timers may be used to generate clock signals needed in the ECG amplifier and the TOCO transducer excitation circuitry. One timer in count mode, together with an external first-order sigma-delta modulator, can be used to form an analog-to-digital converter for the uterine activity signal.

The wireless ultrasound transducer 502 may also include an amplifier 528, e.g., connected to electrodes affixed to the patient, for amplifying signals, In some embodiments, the wireless ultrasound transducer 502 may further include an analog filter 530 to isolate and identify any pre-selected frequency range including fetal heart and fetal brain electrical signal. In some embodiments, the wireless ultrasound transducer 502 may include one or more analog-to-digital converters 511 for receiving an analog input from amplifier 528 and/or directly from the electrodes affixed to the patient. The analog-to-digital converter(s) 511 may be used in some instances to monitor the battery voltage of a power supply 532 of the wireless ultrasound transducer 502, as well as to measure the ultrasound Doppler or ECG signal amplitude to control the signal gain, measure the fetal movement signal amplitude, and to measure some test voltages during the power-up self-tests.

In some embodiments, the pregnancy monitoring system 500 is configured to eliminate noise from the one or more input signals from a remote ultrasound transducer and to analyze the frequency, duration, amplitude, and power density spectrum of the received signals, as well as perform data analysis using techniques such as wavelet transform, Fourier transform, zero-crossing, Wigner-Ville or Heisenberg-Gabor analysis, and time-frequency analysis.

In one embodiment, the fetal monitor receives the raw data collected by the EMG and fetal heart rate monitor, processes the data, and performs data analysis. In still another embodiment, the fetal monitor is or is connected to a wearable device, mobile phone, tablet, laptop computer, local or remote server, or the like. In another embodiment, after the received data have been processed and analyzed by the fetal monitor, it wirelessly transmits the analyzed data back to the patient via the patient's mobile device for visual or audio presentation of the output on the patient's mobile device. In addition, vital patient information, for example age, date of conception, comorbidities, prior pregnancy history, and other medical data parameters may be inputted into the remote device to allow data interpretation or presentation to be customized and adapted based on the patient's medical history or preferences.

In one embodiment of the present disclosure, an electronic display coupled to the electronic circuit allows the display of a patient's current pregnancy status based on the EMG signal and the FHR signal. The apparatus may further include an audio transducer coupled to the electronic circuit, the audio transducer being configured to provide an audible indication of the most recent pregnancy status based on the EMG and FHR signals. In one example embodiment, the transducer comprises an audio speaker for emitting a tone or recorded message.

In addition, by incorporating the capability of remote transmission of data to the treating physician, the patient's treating physician may be provided access to the data of a remote patient wearing the device in real-time or near real-time for rapid analysis of sensor data collected from the patient. This rapid access to data from a remote patient may enable doctors and health care providers to provide the end user with more accurate advice on whether or not to present to the hospital, avoiding false alarms and missed alarms.

In one embodiment, the fetal heart rate signal (ultrasound Doppler or ECG) is wirelessly transmitted using standard direct FM modulation. The uterine activity signal, along with data relating to, for example, power or battery status, transmitter ID, and transducer modes (e.g., ultrasound, ECG, intra-uterine pressure catheter, external tocodynamometry) are transmitted as a digital bit stream. The transmitter serial number, which is preferably the same for both the transmitter and the corresponding receiver, is used by the receiver to synchronize itself with the data stream and to verify that the data is coming from the transmitter paired with it. This prevents or minimizes interference from another transmitter using the same RF frequency. The digital data stream, which may be transmitted as a frequency shift keying ("FSK") signal, for example, can be used to frequency modulate the RF carrier. The amplitude of the composite signal determines the required RF bandwidth. Modulation circuits are used to control the RF bandwidth having a corresponding amplitude and frequency characteristics. The modulation circuits may also be used to optimize available RF bandwidth to get the highest S/N ratio for the transmitted signals.

In one aspect of the disclosure, a programmable-gain amplifier adjusts the heart rate signal amplitude to a value that corresponds to a certain percentage of the maximum allowable RF bandwidth. The remaining RF bandwidth is used to accommodate the often rapidly-changing signal amplitude, especially for the ultrasound Doppler signal. The gain of the amplifier is controlled by a regulator algorithm. The current signal amplitude is measured with one of the integrated A-to-D converter channels, and from this value an appropriate gain is calculated for the programmable-gain amplifier. To prevent the gain from changing too much during one heart period, which could lead to a wrong heart rate calculation for the affected beat, each new gain value is adjusted linearly over a certain period, e.g., over a period of 2 seconds.

The present disclosure is not intended to be restricted to the several exemplary embodiments of the disclosure described above. Other variations that may be envisioned by those skilled in the art are intended to fall within the disclosure.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be understood that certain expressions and reference signs used in the claims pursuant to Rule 6.2(b) of the Patent Cooperation Treaty ("PCT") do not limit the scope.

The invention claimed is:

1. A method for dynamically adjusting sound data compression level and transmission bandwidth of a wireless ultrasound transducer configured to be portable by a patient for wireless health monitoring, the method comprising:
    detecting an ultrasound signal using the wireless ultrasound transducer;
    calculating a distance between the wireless ultrasound transducer and a base station of a wireless health monitoring system based on one or more attributes of a wireless communication channel between the wireless ultrasound transducer and the base station;
    determining a data compression level for compressing data to be transmitted wirelessly from the wireless ultrasound transducer to the base station, based on the distance between the wireless ultrasound transducer and the base station, wherein the data represents the detected ultrasound signal;
    compressing the data that represents the detected ultrasound signal based on the determined data compression level to generate a compressed ultrasound data signal;
    determining, based at least in part on the determined data compression level, the transmission bandwidth for the wireless ultrasound transducer;
    transmitting the compressed ultrasound data signal from the wireless ultrasound transducer to the base station using the determined transmission bandwidth; and
    rendering, by the base station, a synthetic audio representative of the detected ultrasound signal in lieu of the detected ultrasound signal in response to a determination that the determined data compression level satisfies a threshold.

2. The method of claim 1, further comprising rendering, by the base station, a synthetic audio in lieu of the detected ultrasound signal, in response to a determination that a predetermined number of bit errors are detected by the base station.

3. The method of claim 2, further comprising:
    unpacking, at the base station, the compressed ultrasound data signal.

4. The method of claim 3, further comprising:
    determining whether the determined data compression level satisfies a threshold or a determining whether the predetermined number of bit errors are detected by the base station.

5. The method of claim 4, wherein a data compression level for a current transmitter-receiver distance is selected from a previously-stored reference compression level corresponding to a transmitter-receiver distance closest to the current transmitter-receiver distance.

6. The method of claim 1, wherein a data compression level for a current transmitter-receiver distance is selected from a previously-stored reference compression level corresponding to a transmitter-receiver distance closest to the current transmitter-receiver distance.

7. The method of claim 1, wherein the transmission of the compressed ultrasound data signal is terminated when one or more bit errors are detected by the base station.

8. The method of claim 1, wherein the distance between the wireless ultrasound transducer and the base station is based on a received signal strength ("RSS") or a signal time of flight ("TOF").

9. The method of claim 1, wherein said determining the transmission bandwidth includes selecting one or more sub-bands from a plurality of sub-bands based on the determined data compression level, and said transmitting the compressed ultrasound data signal comprises transmitting the compressed ultrasound data signal from the wireless ultrasound transducer to the base station using the selected one or more sub-bands.

10. The method of claim 1, wherein said determining of the data compression level is performed by the wireless ultrasound transducer, and wherein the method further comprises:
    digitizing, by the wireless ultrasound transducer, the compressed ultrasound data signal prior to transmitting the compressed ultrasound data signal to the base station; and
    transmitting the data compression level determined by the wireless ultrasound transducer to the base station.

11. A non-transitory computer readable medium comprising instructions executable by one or more processing units, wherein the instructions, when executed by the one or more processing units, cause the one or more processing units to carry out a method as defined in claim 1.

12. A wireless ultrasound transducer, which is portable by a patient to be monitored and configured to communicatively couple to a base station of a wireless health monitoring system, the wireless ultrasound transducer comprising:
    a transmitter; and
    a processor configured to:
        calculate a distance between the wireless ultrasound transducer and the base station based on one or more attributes of a wireless communication channel between the transmitter and a receiver of the base station;

determine a data compression level for compressing ultrasound data to be transmitted from the wireless ultrasound transducer to the base station based on the distance between the wireless ultrasound transducer and the base station;

compress the ultrasound data to be transmitted based on the determined data compression level to generate a compressed ultrasound data signal;

dynamically adjust, based at least in part on the determined data compression level, a transmission bandwidth of the wireless ultrasound transducer such that the transmitter transmits wirelessly the compressed ultrasound data signal from the wireless ultrasound transducer to the base station using the adjusted transmission bandwidth; and rendering a synthetic audio representative of a detected ultrasound signal in lieu of the detected ultrasound signal by the base station, in response to a determination that the determined data compression level satisfies a threshold.

13. The wireless ultrasound transducer according to claim 12, wherein the transmitter is further configured to transmit data indicative of the determined data compression level to the receiver together with the compressed ultrasound data signal.

14. The wireless ultrasound transducer according to claim 12, further comprising a memory for storing a plurality of reference compression levels corresponding to respective transmitter-receiver distances wherein the processor is configured to select the data compression level from the plurality of reference compression levels by selecting a reference compression level corresponding to a transmitter-receiver distance closest to a current transmitter-receiver distance.

15. A health monitor base station of a wireless ultrasound health monitoring system, comprising:

a receiver configured to receive wirelessly a compressed data signal representative of an ultrasound signal obtained by a transducer of a wireless ultrasound transducer configured to be attached to and worn by a patient for wireless monitoring, wherein a data compression level of the compressed data signal is selected from a plurality of data compression levels based on a distance between the wireless ultrasound transducer and the base station; and a processor configured to render synthetic audio representative of the obtained ultrasound signal in lieu of the ultrasound signal in response to a determination that the selected data compression level satisfies a predetermined threshold.

16. A method for dynamically adjusting sound data compression level and transmission bandwidth of a wireless ultrasound transducer configured to be portable by a patient for wireless health monitoring, the method comprising:

detecting an ultrasound signal using the wireless ultrasound transducer;

calculating a distance between the wireless ultrasound transducer and a base station of a wireless health monitoring system based on one or more attributes of a wireless communication channel between the wireless ultrasound transducer and the base station;

determining a data compression level for compressing data to be transmitted wirelessly from the wireless ultrasound transducer to the base station, based on the distance between the wireless ultrasound transducer and the base station, wherein the data represents the detected ultrasound signal;

compressing the data that represents the detected ultrasound signal based on the determined data compression level to generate a compressed ultrasound data signal;

determining, based at least in part on the determined data compression level, the transmission bandwidth for the wireless ultrasound transducer;

transmitting the compressed ultrasound data signal from the wireless ultrasound transducer to the base station using the determined transmission bandwidth; and rendering a synthetic audio representative of the detected ultrasound signal in lieu of the detected ultrasound signal by the base station, in response to a determination that a predetermined number of bit errors is detected.

17. A wireless ultrasound transducer, which is portable by a patient to be monitored and configured to communicatively couple to a base station of a wireless health monitoring system, the wireless ultrasound transducer comprising:

a transmitter; and a processor configured to:

calculate a distance between the wireless ultrasound transducer and the base station based on one or more attributes of a wireless communication channel between the transmitter and a receiver of the base station;

determine a data compression level for compressing ultrasound data to be transmitted from the wireless ultrasound transducer to the base station based on the distance between the wireless ultrasound transducer and the base station;

compress the ultrasound data to be transmitted based on the determined data compression level to generate a compressed ultrasound data signal;

dynamically adjust, based at least in part on the determined data compression level, a transmission bandwidth of the wireless ultrasound transducer such that the transmitter transmits wirelessly the compressed ultrasound data signal from the wireless ultrasound transducer to the base station using the adjusted transmission bandwidth; and rendering a synthetic audio representative of a detected ultrasound signal in lieu of the detected ultrasound signal by the base station, in response to a determination by the receiver that a predetermined number of bit errors is detected.

18. A health monitor base station of a wireless ultrasound health monitoring system, comprising:

a receiver configured to receive wirelessly a compressed data signal representative of an ultrasound signal obtained by a transducer of a wireless ultrasound transducer configured to be attached to and worn by a patient for wireless monitoring, wherein a data compression level of the compressed data signal is selected from a plurality of data compression levels based on a distance between the wireless ultrasound transducer and the base station; and a processor configured to render synthetic audio representative of the obtained ultrasound signal in lieu of the ultrasound signal in response to a determination by the receiver that a predetermined number of bit errors is detected.

* * * * *